United States Patent [19]

Mechoulam et al.

[11] Patent Number: 4,707,559
[45] Date of Patent: Nov. 17, 1987

[54] ANALGETIC AND ANTIEMETIC COMPOSITIONS

[76] Inventors: Raphael Mechoulam, 12 Tchernikhovsky St., Jerusalem; Jeffery J. Feigenbaum, 7/2 Ben Gavriel St., Talpiot, Jerusalem, both of Israel

[21] Appl. No.: 870,154

[22] Filed: Jun. 3, 1986

[30] Foreign Application Priority Data

Jun. 11, 1985 [IL] Israel ......................................... 75480

[51] Int. Cl.$^4$ ..................... C07C 43/21; A61K 31/085
[52] U.S. Cl. ................................................... 568/644
[58] Field of Search .......................... 568/644; 514/719

[56] References Cited

U.S. PATENT DOCUMENTS 4,391,827  6/1983  Harbert et al. ................. 514/719 X

FOREIGN PATENT DOCUMENTS 0048572  3/1982  European Pat. Off. ............ 514/719

Primary Examiner—Werren B. Lone
Attorney, Agent, or Firm—Fleit, Jacobson, Cohn & Price

[57] ABSTRACT

There are provided 3-(6-alkoxy-4-alkyl-2-hydroxyphenyl) cyclohexanol derivatives and pharmaceutical compositions containing these as active ingredient. These are useful as potent analgesics and also as antiemetics. The compounds have the advantage of being devoid of psychotropic activity.

12 Claims, No Drawings

ANALGETIC AND ANTIEMETIC COMPOSITIONS

FIELD OF THE INVENTION

There are provided certain novel 3-[6-alkoxy-4-alkyl-2-hydroxy phenyl]-cyclohexanol derivatives. The compounds of the invention are potent analgetics and antiemetics essentially devoid of psychotropic activity.

BACKGROUND OF THE INVENTION

There are known similar compounds such as 3-[2-hydroxy-4-alkylphenyl]-cyclohexanols, but these have the serious drawback of simultaneous psychotropic activity: see A. Weissman et al., J. Pharmacol. Exp Ther 223, 516 (1982)(ref 8). The effect of respiratory depression which is present with morphine type compounds is also absent with compounds of the present invention.

SUMMARY OF THE INVENTION

According to the present invention there are provided novel compounds of the general formula

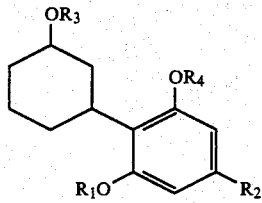

wherein
   $R_1$ designates straight or branched alkyl of up to and including 5 carton atoms.
   $R_2$ designates alkyl of 5 to 12 carbon atoms
   $R_3$ and $R_4$, which may be identical or different, each designates hydrogen or an easily cleavable group such as esters of fatty acids (acetic, propionic, butyric, etc.) wherein the cyclohexyl moiety can be further substituted by non-interfering substituents.

The compounds of choice are the ones with both $R_3$ and $R_4$ designating hydrogen. The products are generally obtained as a mixture of the E-and Z-configuration isomers, with a preponderance of the Z isomer. The invention relates to the mixture of the isomers as well as to the individual isomers.

The compounds of the invention have a pronounced analgetic and antiemetic effect. They can be administered by the oral route, by injection or suppositories.

The effective dosage is of the order of 0.01 mg/kg patient weight to about 1.0 mg/kg patient weight per unit dosage form. The novel compounds are essentially devoid of undesired psychotropic side effects, and furthermore they do not bring about a depression of respiration.

The novel analgetic compositions have a potency similar to that of opioids, and such high activity has not been observed hitherto with nitrogen free compounds except for the Weissman compounds mentioned about which are also N-free.

The compounds of the invention can be prepared according to the following reaction scheme:

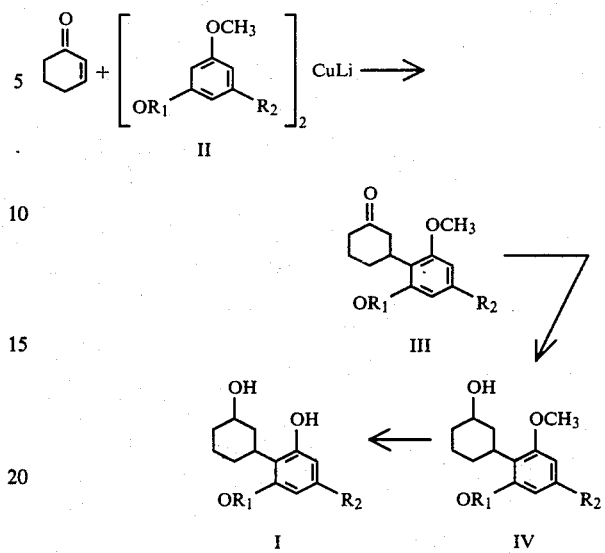

$R_1$ and $R_2$ are as noted above.

The appropriate 1-methoxy-3-alkyl-5-alkoxy benzenes (II) on reaction with butyl lithium give the lithium derivatives of II, which without isolation are reacted upon with cuprous bromide to give the copper-lithium derivatives of II. Comparable copper lithium derivatives of resorcinol diethers, though not of mixed resorcinol diethers have previously been reported (cf ref 1). The copper-lithium derivative of II, which was not isolated, was reacted with cyclohexenone to yield racemic compounds of type III, namely the appropriate 3-[2-methoxy-4-alkyl-6(alkoxy)phenyl]cyclohexanones. Compounds of type III on reduction with $NaBH_4$ gave a mixture of the racemic (E) and (Z) alcohols of type IV, namely the appropriate (E) and (Z) -3-[2-(methoxy)-4-alkyl-6-(alkoxy)phenyl]-cyclohexanols (IV). The predominant isomer, is that in which the hydroxyl group and the aryl group are cis (i.e. the compounds in the Z series).

The compounds of type I were obtained by demethylation of the appropriate IV with sodium hydride in propylmercaptane in hot dimethyl formamide. Under these conditions the methyl ether is cleaved in preference to higher alkyl ethers. In the case of dimethylethers of type IV (i.e. $R_1=CH_3$) only one ether group is demethylated.

Pharmacology:

The new compounds described above were evaluated pharmacologically by standard tests, namely for analgesia the acid-induced writhing in mice (2), tail immersion in rats (4), tail flick in rats (5) and yeast paw in rats (3). The activity of the compounds in the first three tests was compared to that of morphine. The $MPE_{50}$ (the dose needed to produce 50% of the maximum possible effect) of compounds Ia and Id are presented in Table 1. Examples of the rest of the compounds (in the writhing test alone) are presented in Table II.

The method used for evaluating the effectiveness of the compounds against emesis induced by apomorphine and cis-platinum was taken from Koster, 1956 (ref. 9).

At 2.0 mg/kg i.v. in pigeons compound Ia prevented all vomiting induced by 8 to 20 mg/kg ip apomorphine or cis-platinum. Compound Ia prevented the lethal effect of cis-platinum in pigeons which is observed as a delayed effect when the latter was injected at a dose ≧20mg/kg.

The existence of possible undesirable psychotropic effects of the new compounds were tested by the ring test (6) which is a quantitative method for assessing the cataleptic effect of Cannabis in mice. The results of this (with several of the new compounds) test presented in Table III.

All compounds tested were dissolved in 5% Emulphor, 5% ethanol (99% pure) and 90% saline. If the saline used contained a molar equivalent of $CuBr_2$ to the compound tested the activity is significantly increased (33–50%). The data presented in this patent is therefore that obtained with the $CuBr_2$ containing vehicle. The vehicle (with or without $CuBr_2$) alone produces no analgesia or has any antiemetic effect and does not differ in activity from saline.

Discussion:

Several of the new compounds of type I were shown to exhibit potent analgetic activity (see Table I) in the dose range usually observed with opioids but not with nitrogen-free compounds. In several tests the most potent compound in the present series, namely Ia, was considerably more potent than morphine. In a standard test for psychotropic activity (the ring test) several of the analgetically active compounds showed complete inactivity. This observation is of considerable importance as a group of related compounds, cf.V, which show considerable analgetic activity[7] also show psychotropic activity[8] and hence their usefulness as drugs is much diminished.

An important observation is that compounds of type I prevent vomiting induced by apomorphine or by cis-platinum.

A further observation of therapeutic importance is that the compounds of type I show no respiratory depression when tested in rabbits. Such an effect is observed with morphine and represents a side effect which limits opinoid use.

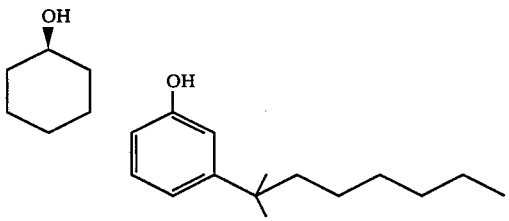

V

EXAMPLES

3-[2-(methoxy)-4-(1,1-dimethylheptyl)-6-(ethoxy)-phenyl]-cyclohexanone (IIIa)

1-Methoxy-3-(1,1-dimethylheptyl)-5-ethoxybenzene (IIa) (1500 mg, 5.4 mmol) was dissolved in dry ether (25 ml) and the solution was cooled to 0° C. The reaction was placed under nitrogen and butyl lithium (5.94 mmol, 3.6 ml of a solution in hexane) was injected into the reaction. The reaction mixture was brought to room temperature, and was stirred for 4 hrs. Cuprous bromide (360 mg, 2.5 mmol) was added in one portion. The reaction mixture turned dark and became homogeneous. After stirring for 5 min, 2-cyclohexanone (240 mg, 2.5 mmol) was injected into the solution, and the reaction mixture was stirred for 15 min at 0°. Ether (50 ml) and a saturated ammonium chloride solution (150 ml) were added. The organic layer was washed with brine, dried and evaporated to dryness. The oil obtained was purified by medium pressure liquid chromatography (230–400 mesh ASTM, silica gel 60″ for column chromatography; elution with petroleum ether, b.p. 60°–80°) to yield the title compound, IIIa (66%).

UVmax (EtOH) 272 ($\epsilon$1410), 279sh nm (1350);

NMR $\delta$(CDCl$_3$), 0.88(3H,t,CH$_3$), 1.25 (2X3H,s,CH$_3$),1.59 (3H,t.CH$_3$), 3.46 (1H,brt, J=3H$_z$, C-3H), 3.77 (3H,s,OCH$_3$), 4.01 (2H q J=5H$_z$, methylene H); 6.47 (2H,s,arom.H);

MS(20°),m/e 394 (m$^+$,2), 356(6), 342(8), 294(16), 258(8), 209(100);

IR(film), 2910, 2845,1710, 1600, 1576, 1445, 1410,1238,1220,1120 cm$^{-1}$.

(Z)-3-[2-(Methoxy)-4-(1,1-dimetheylheptyl)-6-(ethoxy)-phenyl]cyclohexanol (IVa)

Compound IIIa(566 mg, 1.5 mmol) was dissolved in dry tetrahydrafuran (0.5 ml). Absolute ethanol (5 ml) was added to the solution. The reaction mixture was cooled to −40°, and NaBH$_4$ (113 mg, 3 mmol) was added. The reaction was stirred for 15 min at −40°, allowed to warm to −10° and then quenched by the addition of water (100 ml). Ether (50 ml) was added, the organic layer was separated, dried (MgSO$_4$) and evaporated to dryness. The reaction product was separated by medium pressure liquid chromatography (elution with ethyl acetate-petroleum ether 2.5 : 97.5) to yield the title compound (IVa), 52% yield, m.p. 44–6.

UVmax (EtOH, 272 ($\epsilon$710), 279nm (640);

NMR $\delta$(CDCl$_3$), 0.89 (3H,t,CH$_3$), 1.26 (2×3H,brs,CH$_3$), 1.66 (3H,t,CH$_3$), 3.40 (1H,m,C-3H), 3.78 (3H,brs,OCH$_3$), 3.96 (2H,q,J=4 Hz,methylene H), 4.60 (1H,brs,OH), 6.48 (2H,brs,arom H);

MS(20°), m/e 376(M+50), 358(6), 320(9), 306(9), 292(94), 291(100), 288(13), 207(8), 193(22);

IR(film), 3360, 2930, 2870, 1610, 1576, 1455, 1419, 1370, 1240, 1190, 1128, 1096, 1045 cm$^{-1}$.

Z-3-[6-(Ethoxy)-4-(1,1-dimethylheptyl)-2-hydroxy phenyl]-cyclohexanol (Ia)

Dimethylformamide (10 ml) was added under nitrogen to sodium hydride (50%) (177 mg, 7.37 mmol), previously washed with petroleum ether. The reaction vessel was cooled to 0°, propylmercaptane (0.62 ml, 6.7 mmol) was added slowly via a syringe. After the reaction had subsided (ca 5 min) the reaction mixture was brought to room temperature, and compound (IVa) (254 mg, 0.67 mmol) in dimethyl formamide (1 ml) was added. The reaction was boiled under reflux for 2 hrs, cooled, poured over 1N hydrochloric acid (100 ml) and extracted with ether (50 ml). The organic extract was washed with water, dried (MgSO$_4$) and evaporated. Pentane was added to the residue and compound (Ia) precipitated out, m.p. 96° C., yield 74%.

UVmax (EtOH), 271 ($\epsilon$1170), 281nm (1110);

NMR $\delta$(CDCl$_3$), 0.83(3H,t,CH$_3$), 1.20(2×3H,s,CH$_3$), 1.33(3H,t, J=6 8 Hz, CH$_3$), 1.87(2H,q,J=7 Hz,methylene H), 4.85(1H,s,OH), 6.28(1H,d,J=2 Hz,arom H), 6.39(1H,d,J=2 Hz,arom H);

MS(20°), m/e 362(M+28), 344(15), 302(14), 277(32), 260(100);

IR(film), 3450, 2940, 2870, 1618, 1590, 1450, 1420, 1365, 1325, 1235, 1195, 1120, 1075, 1048, 962, 840 cm$^{-1}$.

Anal. calcd: C$_{23}$H$_{38}$O$_3$, C,76.24; H,10.49; Found: C,76.30; H, 10.34.

3-[2-(Methoxy)-4-(pentyl)-6-(ethoxy)phenyl]-cyclohexanone (IIIc)

When the procedure described for the preparation of IIIa (see above) is followed, except that 1-methoxy-3-pentyl-5-ethoxy benzene, rather than the 3-(1,1-dimethyl heptyl) homolog is used we obtained the title compound IIIc, (54%).

UVmax (EtOH), 272 ($\epsilon$1320), 279nm (1270);

NMR $\delta$(CDCl$_3$), 0.89(3H,t,CH$_3$), 1.39(3H,t,CH$_3$), 2.53(2H,t,benzylic H), 3.18(1H,t,J=12 Hz, C-3H), 3.76(3H,s,OCH$_3$) 4.01(2H,q,J=6 Hz, methylene H), 6.34(2H,s,arom H);

MS(20°), m/e 318(M+, 93), 287(21), 273(14), 261(100), 247(29), 235(21);

IR(film), 2920, 2860, 1700, 1525, 1425, 1365, 1340, 1308, 1233, 1210, 1188, 1110, 1072, 810 cm$^{-1}$.

3-[2,6-(dimethoxy)-4-(pentyl)-phenyl]-cyclohexanone (IIIb)

When the procedure described for the preparation of IIIa (see above) is followed except that 1,5-dimethoxy-3-pentyl benzene, rather than 1-methoxy-3-(1,1-dimethyl heptyl)-5-ethoxy benzene, is used we obtained the title compound (IIIb), (38%), m.p. 66°-68° C.;

UVmax (EtOH), 272 ($\epsilon$1690), 279sh nm (1610);

NMR $\delta$(CDCl$_3$) 0.91(3H,tCH$_3$), 2.44(2H,t,benzylic H), 3.78(2×3H,s,OCH$_3$), 6.37(2H,s,arom H);

MS(20°), m/e 304(M+, 71), 273(24), 261(27), 247(100), 221(22);

IR(Nujol), 1689, 1599, 1569, 1445, 1410, 1360, 1228, 100 cm$^{-1}$.

Anal. Calcd; C$_{19}$H$_{28}$O$_3$, C, 75.00; H,9,21; Found: C,75.10, H,9.34.

3-[2,6 -Dimethoxy-4-(1,1-dimethyl heptyl)-phenyl]-cyclohexanone (IIId)

When the procedure described for the preparation of IIIa (see above) is followed except that 1,5-dimethoxy-3-(1,1-dimethyl heptyl) benzene, rather than 1-methoxy-3-(1,1-dimethyl heptyl)-5-ethoxy benzene is used we obtained the title compound (IIId), (35%), m.p. 64°-65° C.;

UVmax (EtOH), 272 ($\epsilon$1300), 278nm (1280);

NMR $\delta$(CDCl$_3$), 0.94(3H,t,CH$_3$), 1.28(2×3H,s,CH$_3$), 3.79(2×3H,s,OCH$_3$), 6.49(2H,s,arom H);

MS(20°), m/e 360(M +, 50), 303(23), 276(87), 275(100);

IR(Nujol), 1706, 1600, 1520, 1445, 1408, 1365, 1312, 1238, 1218, 1192, 1172, 1105, 1095, 1022, 970, 825, 712, 672 cm$^{-1}$.

Anal. Calcd; C$_{23}$H$_{36}$O$_3$, C,76.67; H, 10.00; Found: C,76.74; H,9.78

(E) and (Z)-3-[2, 6-dimethoxy-4-(1,1-dimethyl heptyl)-phenyl]-cyclohexanol (IVg and (IVd)

When the procedure described for the preparation of IVa (see above), except that IIId rather than IIIa is used, we obtained a mixture of IVg and IVd. These two isomers were separated by column chromatography to give pure IVg, (5% ), m.p. 77°-78° C.;

UVmax (EtOH), 271 ($\epsilon$1240), 277sh nm (1150);

NMR $\delta$(CDCl$_3$) 0.87(3H,t,CH$_3$), 1.30(2×3Hs,CH$_3$), 3.82(2×3H,s,OCH$_3$), 4.19(1H,br,OH), 6.52(2H,s,arom H);

MS(20°), m/e 362(M+, 47), 344(37), 290(25), 277(100), 259(42);

IR(Nujol), 3580, 1572, 1443, 1411, 1376, 1240, 1225, 1195, 1176, 1086, 968, 825 cm$^{-1}$.

and IVd, (67%), m.p. 74°-75° C.;

UVmax (EtOH), 272 ($\epsilon$960), 278sh nm (850);

NMR $\delta$(CDCl$_3$), 0.83(3H,t,CH$_3$), 1.27(2×3H,s,CH$_3$), 3.78(2×3H,s,OCH$_3$), 6.48(2H,s,arom H):

MS(100°), m/e 362(M+, 52) 344(11), 306(9), 277(100);

IR(Nujol), 2890, 1570, 1442, 1406, 1370, 1315, 1235, 1185, 1119, 1050, 952, 820 cm$^{-1}$.

Anal.Calcd; C$_{23}$H$_{38}$O$_3$, C,76.24; H, 10.50; Found: C76.23, H,10.45.

(E) and (Z)-3-[2-methoxy-4-pentyl-6-ethoxy phenyl]-cyclohexanol (IVf and IVc)

When the procedure described for the preparation of IVa (see above) except that IIIc rather than IIIa is used, we obtained a mixture of IVf and IVc. These two isomers were separated by column chromatography to give pure IVf, (5.9%), UVmax (EtOH), 271 ($\epsilon$1070), 278sh nm (1900);

NMR $\delta$(CDCl$_3$), 0.85(3H,t,CH$_3$), 1.35(3H,q,J=7 Hz, (H3), 256(2H,t, benzylic H), 3.71 (3H,s,OCH$_3$), 3.95(2H,q,J-7 Hz methylene H), 6.29(2H,s, arom H);

MS(20°), m/e 320(M+, 77), 302(54), 273(25), 235(100), 223(27);

IR(film), 3400, 2915, 2850, 1605, 1575, 1420, 1395, 1216, 1189, 1080, 970, 808 cm$^{-1}$.

and IVc, (76%),

UVmax (EtOH), 271 ($\epsilon$1000), 278sh nm 890);

NMR $\delta$(CDCl$_3$ ), 0.87(3H,t,CH$_3$), 1.26(3H,t,J=6 Hz,CH$_3$), 2.53(2H,t,benzylic H), 3.74 (3H,s,OCH$_3$), 3.97(2H,q,J=7 Hz)methylene H), 6.33(2H,s, arom H);

MS(20°), m/e 320(M+, 93), 302(24), 277(19), 264(22), 235(100);

IR(film), 3350,2910,2830,1605,1579,1448,1423,1390,1362, 1220, 1190, 1113, 1043, 955, 810 cm$^{-1}$.

(E) and (Z)-3-[2,6-dimethoxy-4-pentyl-phenyl]-cyclohexanol (IVe and IVb)

When the procedure for the preparation of IVa (see above), except that IIIb rather than IIIa, is used we obtained a mixture of IVe and IVb. These two isomers were separated by column chromatography to give IVe ( 7% ), UVmax (EtOH), 273 ($\epsilon$920), 280sh nm (730);

NMR $\delta$(CDCl$_3$), 0.94(3H,t,CH$_3$), 2.56(2H,t,benzylic H), 3.66(1H,m,C-1H), 3.76(2×3H,s,OCH$_3$), 4.18(1H,brs,OH), 6.35(2H,s,arom H);

MS(20°), m/e 306(M+, 100), 287(89, 273(14), 260(30), 250(19),222(22);

IR(Nujol), 3410, 1594, 1568, 1436, 1365, 1210,1116, 1094, 1075, 955, 803 cm$^{-1}$. m.p. 65°-66° C.;

Anal.Calcd; C$_{19}$H$_{30}$O$_3$, C,74.51; H,9.80; Found; C,74.67; H,9.96.

and IVb, (74 %), m.p. 71°-72° C.;

UVmax (EtOH), 271 ($\epsilon$1220), 279sh nm (1090);

NMR $\delta$(CDCl$_3$) 0.93(3H,t,CH$_3$), 2.54(2H,t,benzylic H), 3.23(1H,m,C-3H), 3.67(1H,m,C-1H), 3.77(2×3H,s,OCH$_3$), 6.36(2H,s,arom H);

MS(150°), m/e 306(M+, 79), 288(29), 263(19), 250(15), 222(100);

IR(Nujol), 3360, 1569, 1450, 1410, 1362, 1216, 1180, 1125, 1095, 1035, 799 cm$^{-1}$.

Anal.Calc C$_{19}$H$_{30}$O$_3$, C, 74.50; H,9.80; Found: C,74.72; H,9.74.

(Z)-3-[6-methoxy-4-pentyl-2-hydroxy phenyl]-cyclohexanol (Ib)

When the procedure for the preparation of Ia is followed, except that IVb rather than IVa is used we obtained the title compound Ib, (63%), m.p. 142°-144° C.; UVmax (EtOH), 272(ε1200), 280nm (1110);

NMR δ(CDCl$_3$), 0.88(3H,t,CH$_3$), 2.47(2H,t,benzylic H), 31.6(1H,m, C-3H), 3.70(1H,m,C-1H), 3.76(3H,s,OCH$_3$), 5.08(1H,brs,OH), 6.18(1H,s,arom H); 6.28(1H,s,arom H);

MS(20°), 306(M+, 5 ), 292(32, 274(44), 246(15), 231(27), 218(100);

IR(nujol), 3480, 3290, 1598, 1579, 1505, 1445, 1412, 1365, 1220, 1165, 1076, 1020, 945, 800 cm$^{-1}$.

(Z)-3-[6-Ethoxy-4-phenyl-2-hydroxyphenyl]-cyclohexanol (Ic)

When the procedure for the preparation of Ia is followed except that IVc rather than IVa is used, we obtained the title compound Ic, (38 %).

UVmax (EtOH), 273 (ε1190), 280nm (1120);

NMR δ(CDCl$_3$), 0.89(3H,t,CH$_3$), 1.39(3H,t,J=6 Hz,CH$_3$), 2.45(2H,t,benzylic H), 3.97 (2H, q, J=6 Hz,metylene H), 6.16(1H,brs, arom H), 6.21(1H,brs, arom H);

MS(20°), m/e 306(M$^{30}$, 39), 280(47), 260(15), 259(16), 245(27),232(100);

IR(film), 3320, 2908, 2838, 1604, 1576, 1500, 1420, 1345, 1105, 1056, 1030 cm$^{-1}$.

Z-3-[6-methoxy-4-(1,1-dimethyl)-2-hydroxyphenyl-]-cyclohexanol (Id)

When the procedure for the preparation if Ia is followed (see above), except that IVd rather than IVa is used we obtained the title compound Id, (83%), m.p. 142°-144°C., UVmax (EtOH) 272 (ε1310), 279nm (1250);

NMR δ(CDCl$_3$), 0.85(3H,t,CH$_3$), 1.23(2×3H,s,CH$_3$), 3.78(3H,s,OCH$_3$), 4.91(1H,br,OH), 6.30(1H,d,J=2 Hz,arom H), 6.42(1H,d,J=2 Hz,arom H);

MS(120°), m/e 348(M+, 29), 330(19), 288(12), 276(16), 263(33), 246(100);

IR(Nujol), 3450, 3270, 2930, 2870, 1585, 1450, 1418, 1384, 1245, 1178, 1123, 1085, 1028, 961, 850, 825 cm$^{-1}$.

Anal. Calcd; C$_{22}$H$_{36}$O$_3$, C, 75.86; H,10.34; Found; C,76.10; H, 10.24;

References

1. J. M. Luteijn et al., *J. Chem. Soc., Perkin I*, 201 (1979).
2. R. M. Koster et al., *Fed. Proceed.* 18, 412 (1959): R. D. Sofia et el., *J. Pharmacol. Exp. Ther.*, 186, 646 (1973).
3. L. O. Randall and J. J. Selitto, *Arch. Int. Pharmacodyn.*, 61, 409(1957).
4. P. A. J. Jenssen et al., *Arzneim Forsch.*, 13, 502–508 (1963).
5. M. Grotto et al., *Arch. Int. Pharmacodyn.*, 170, 257 (1967).
6. R. G. Pertwee, *Brit. J. Pharmacol.*, 46, 753 (1972).
7. L. S. Melvin et al., *J. Med. Chem.*, 27, 67 (1984).
8. A. Weissman et al., *J. Pharmacol. Exp. Ther.*, 223, 516 (1982).
9. R. Koster, *Pharmacol. Rev.*, 8, 406 (1956).

| Analgetic Effects of Compounds Ia and Id MPE$_{50}$ mg/kg (n = 10) | | | | |
|---|---|---|---|---|
| Compound | writhing (2)* (mice) | tail immersion (4)* (rats) | yeast paw (3)* (rats) | tail flick (5)* (rats) |
| morphine | 0.1 (sc) | 10.0 (sc) | | 6.0 (sc) |
| Ia | 0.01 (sc) | 1.5 (sc) | 1.5 (sc) | 1.5 (sc) |
| Id | 0.05 (sc) | 5.0 (sc) | 3.0 (sc) | |

*Reference to method

TABLE II

| Examples of Analgetic Effects of Some New Compounds | |
|---|---|
| compound | MPE$_{50}$, mg/kg (n = 10) Writhing (2)* |
| morphine | 1.0 (po) |
| Ib (R$_1$ = CH$_3$; R$_2$ = C$_5$H$_{11}$) | 1.0 (po) |
| Ic (R$_1$ = C$_2$H$_5$; R$_2$ = C$_5$H$_{11}$) | 0.7 (po) |
| Ie (R$_1$ = C$_3$H$_7$; R$_2$ = C$_5$H$_{11}$) | 0.8 (po) |
| If (R$_1$ = C$_4$H$_9$; R$_2$ = C$_5$H$_{11}$) | 4.0 (po) |
| Ig (R$_1$ = CH$_3$; R$_2$ = C$_6$H$_{13}$) | 1.2 (po) |
| Ih (R$_1$ = CH$_3$; R$_2$ = C$_7$H$_{15}$) | 3.2 (po) |
| Ii (R$_1$ = C$_2$H$_5$; R$_2$ = C$_6$H$_{13}$) | 0.02 (po) |
| Ij (R$_1$ = C$_2$H$_5$; R = C$_7$H$_{15}$) | 0.02 (po) |

*Number indicates reference to method.

TABLE III

| | Ring Test* | |
|---|---|---|
| Compound** | Dose (mg/kg, po) | Ring Index |
| control | 0.1 ml/10 gr | 4.9 |
| Δ$^9$-tetrahydro cannabinol | 1.0 | 40 |
| Ia | 5.0 | 5.8 |
| Id | 5.0 | 7.6 |
| Ib | 5.0 | 8.2 |

*method: A mouse is placed upon a metal ring (diameter 5.5 cm). An untreated mouse remains almost continuously active when placed on the ring. A mouse treated with an effective compound will have its continuous movement interrupted by varying lengths of quiet. The percentage time the mouse remains quiet is assessed over a period of 5 mins.
**The compound tested is dissolved in sunflower oil and administered in 0.1 ml/10 gr of body weight.

We claim:
1. A 3- 6-(alkoxy)-4-(alkyl)-2-hydroxy phenyl -cyclohexanol derivative of the general formula

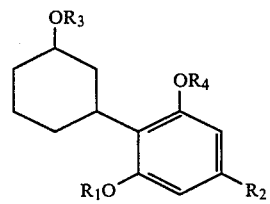

wherein R$_1$ designates straight or branched alkyl of up to and including 5 carbon atoms,
R$_2$ designates alkyl of 5 to 12 carbon atoms,
R$_3$ and R$_4$, which may be identical or different, each designates hydrogen an easily cleavable group giving a hydroxy group and
wherein the cyclohexyl moiety can be further substituted by non-interfering substituents.
2. A compound according to claim 1, wherein R$_3$ and R$_4$ both designate hydrogen.
3. A compound according to claim 1 wherein R$_2$ is selected from pentyl, hexyl, heptyl, 1,1 or 1,2-dimethylheptyl, nonyl and decyl.

4. A compound according to claim 1, in the Z-configuration.

5. A compound according to claim 1, in the E-configuration.

6. A mixture of the E- and Z-isomers of the compounds defined in claim 1.

7. A pharmaceutical composition comprising as active ingredient a compound according to claim 1.

8. A pharmaceutical composition according to claim 7, wherein said active ingredient is an E- or an Z-isomer.

9. An analgetic and/or antiemetic pharmaceutical composition essentially devoid of psychotropic effects, containing an analgetically and/or an antiemetic effective quantity of a compound claimed in claim 1.

10. A pharmaceutical composition according to claim 7, in unit dosage form, containing the active ingredient with a diluent, pharmaceutically acceptable carrier or adjuvant.

11. A pharmaceutical composition containing as active ingredient preponderantly the cis (Z) isomer of a compound claimed in claim 1.

12. A pharmaceutical composition according to claim 7 in unit dosage form, wherein the quantity of the active ingredient varies between 1 mg and 30 mg per such unit dosage form.

* * * * *